United States Patent
Brown et al.

(10) Patent No.: US 10,048,186 B2
(45) Date of Patent: Aug. 14, 2018

(54) OPTICALLY INTERFACED FLUID DENSITY SENSOR

(71) Applicant: Simmonds Precision Products, Inc., Vergennes, VT (US)

(72) Inventors: Rollin W. Brown, South Burlington, VT (US); James C. Averill, North Ferrisburgh, VT (US); Robbie W. Hall, Charlotte, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 223 days.

(21) Appl. No.: 15/074,408

(22) Filed: Mar. 18, 2016

(65) Prior Publication Data

US 2017/0268974 A1    Sep. 21, 2017

(51) Int. Cl.
| | |
|---|---|
| *G01N 9/00* | (2006.01) |
| *G02B 6/42* | (2006.01) |
| *G01N 33/28* | (2006.01) |

(52) U.S. Cl.
CPC ............... *G01N 9/002* (2013.01); *G02B 6/42* (2013.01); *G02B 6/4246* (2013.01); *G01N 33/28* (2013.01); *G01N 2009/006* (2013.01)

(58) Field of Classification Search
CPC .. G02B 6/42; G02B 6/4246; G01N 2009/006; G01N 33/28; G01N 9/36; G01N 9/002; G01N 33/22; G01N 27/221; G01F 23/0061; G01F 23/266

See application file for complete search history.

(56) References Cited

U.S. PATENT DOCUMENTS

| | | | |
|---|---|---|---|
| 3,808,875 A | 5/1974 | Miller | |
| 4,677,305 A | 6/1987 | Ellinger | |
| 4,802,360 A | 2/1989 | Maier | |
| 4,900,921 A | 2/1990 | Spillman, Jr. | |
| 6,076,392 A * | 6/2000 | Drzewiecki | A61M 16/0051 73/23.2 |

(Continued)

FOREIGN PATENT DOCUMENTS

EP     2015371 A1    1/2009

OTHER PUBLICATIONS

Extended European Search Report, for European Patent Application No. 17161513.1, dated Jun. 16, 2017, 10 pages.

*Primary Examiner* — Francis C Gray
(74) *Attorney, Agent, or Firm* — Kinney & Lange, P.A.

(57) ABSTRACT

Apparatus and associated methods relate to suppressing electrical arcing within a fuel tank in which a fuel density sensor is located by isolating electronic components of the fuel density sensor within a cavity surrounded by a dielectric housing. The dielectric housing physically isolates the sensor electronics from fuel in the fuel tank via a fuel barrier. The dielectric housing electrically isolating the sensor electronics within the cavity from potential high voltage hazards outside the cavity. Light energy optically from a first environment outside the cavity is transmitted through the dielectric housing to a second environment within the cavity to provide operating power for the sensor electronics. The light energy is converted into DC electrical energy within the cavity. A light signal indicative of fuel density is optically transmitted from the second environment within the cavity through the dielectric housing to the first environment outside the cavity.

14 Claims, 6 Drawing Sheets

(56) References Cited

U.S. PATENT DOCUMENTS

| | | | |
|---|---|---|---|
| 6,509,566 B1 * | 1/2003 | Wamsley | G01N 21/3504 250/338.5 |
| 6,744,036 B2 | 6/2004 | Kline | |
| 7,259,384 B2 | 8/2007 | Hariram et al. | |
| 7,638,750 B2 | 12/2009 | Kline | |
| 7,965,948 B1 | 6/2011 | Bugash et al. | |
| 2004/0061043 A1 * | 4/2004 | Kline | G01F 23/0061 250/227.21 |
| 2008/0137808 A1 | 6/2008 | James et al. | |
| 2014/0331763 A1 * | 11/2014 | Robb | G01F 23/266 73/304 C |
| 2014/0373622 A1 * | 12/2014 | Kline | B64D 37/005 73/290 R |
| 2015/0053004 A1 * | 2/2015 | Bahorich | G01N 9/002 73/579 |
| 2016/0375985 A1 * | 12/2016 | Ribarov | B64D 37/04 244/135 C |
| 2016/0377587 A1 * | 12/2016 | Kumar | B64D 37/005 73/32 A |

* cited by examiner

OPTICALLY INTERFACED FLUID DENSITY SENSOR

BACKGROUND

The fuel that is used in aircrafts has a density that changes with brand, additives, temperature and pressure, as well as other factors. Because the density of aircraft fuel changes in response to these factors, knowing the volume of fuel aboard an aircraft doesn't always sufficiently inform the pilot of the amount of fuel, and therefore the possible range of flight of the aircraft. The product of fuel volume and fuel density gives the fuel mass, which is a better metric of the amount of fuel carried by the aircraft. Many modern aircrafts are equipped with both fuel volume sensors and fuel density sensors.

Fluid density sensors or fluid densitometers are used to measure the density of a fluid. Such sensors can be constructed to exploit different principles of operation. For example, one of the oldest ways to measure density is by measuring a pressure differential between two bubble tubes vertically oriented in a fluid tank. In this method, the two bubble tubes are immersed in the fluid tank. Each of the bubble tubes extends to a different depth in the fluid tank. Air is pumped through each of the tubes so as to purge the tube of fluid, which results in bubbles being injected at the depth of the bubble tube. The back pressure is measured for each of the bubble tubes. The difference between the back pressures of the two bubble tubes is related to the density of the fluid in the tank.

Other methods of measuring a density of a fluid employ various mechanical oscillation measurements. For example, a spring may oscillate at a first resonant frequency when oscillating in air. But when submersed in a liquid, the spring may oscillate at a second resonant frequency. The resonant frequency of oscillation may be indicative of a density of the fluid in which the spring resides. Other electromechanical oscillators that vibrate at a frequency proportional to the density of the medium surrounding the oscillator can also be used to measure fluid density. A vibrating spool densitometer is one such fluid density transducer. These vibrating spool densitometers traditionally have electrical interfaces, with which to communicate operating power and output signals to a control unit.

Electrically communicating between a control unit outside of a fuel tank and an electromechanical oscillator within a fuel tank can incur risks of electrical arcing, which in turn can ignite the fuel within the tank. A short circuit or a lighting strike involving the electrical lines that connect the fuel density sensor to the controller can have catastrophic consequences. Thus, there is a need for eliminating electrical communications between equipment located within a fuel tank and controllers located outside the fuel tank.

SUMMARY

Apparatus and associated methods relate to a fluid density sensor configured to optically receive operating power and to optically communicate a measured fluid density. The fluid density sensor includes a fluid tight housing separating an interior cavity from an exterior environment. The fluid tight housing is configured to prevent a fluid from the exterior environment entering the interior cavity. The fluid density sensor includes a fiber optic connection port configured to connect to an optical fiber in the exterior environment while providing an optical path for light energy to traverse the fluid tight housing. The light energy is communicated between the optical fiber and the interior cavity. The fluid density sensor includes a fluid density transducer configured to be immersed in the fluid. The fluid density transducer generates an electrical output signal indicative of a density of the fluid. The fluid density sensor also includes sensor electronics located entirely within the interior cavity. The sensor electronics includes an optical power converter configured to convert the light energy communicated from the optical fiber to the optical power converter within the interior cavity via the fiber optic connection port. The light energy is converted into DC electrical energy. The sensor electronics includes an energy storage device configured to store the converted DC electrical energy. The sensor electronics includes a signal generator configured to generate, using at least a portion of the stored DC electrical energy, an electrical input signal for use by the fluid density transducer. The sensor electronics includes a transducer interface configured to supply the generated electrical input signal to the fluid density transducer and to receive the electrical output signal of the fluid density transducer. The sensor electronics also includes an optical signal generator configured to generate a light signal, based on the received electrical output signal, the light signal indicative of the density of the fluid.

Various embodiments relate to a method of suppressing electrical arcing within a fuel tank in which a fuel density sensor is located. The method includes physically isolating sensor electronics from fuel in the fuel tank via a fluid barrier. The method includes electrically isolating the sensor electronics within a cavity from potential high voltage hazards without the cavity. The method includes optically communicating light energy between without the cavity and within the cavity. The method includes converting light energy from without the cavity into DC electrical energy within the cavity. The method includes storing the converted DC electrical energy. The method includes supplying the sensor electronics with operating power from the converted DC electrical energy. The method includes determining a density of a fuel without the cavity. The method also includes generating a light signal indicative of the density of the fluid.

In some embodiments, a vibrating spool densitometer is configured to optically receive operating power and to optically communicate a measured fuel density. The vibrating spool densitometer includes a fuel tight housing separating an interior cavity from an exterior environment. The fuel tight housing is configured to prevent a fuel from the exterior environment entering the interior cavity. The vibrating spool densitometer includes a fiber optic connection port configured to connect to an optical fiber in the exterior environment while providing an optical path for light energy to be communicated from the optical fiber to the interior cavity. The vibrating spool densitometer includes a vibrating spool transducer configured to be immersed in the fuel. The vibrating spool transducer has a resonant frequency indicative of a density of the fuel. The vibrating spool densitometer also includes sensor electronics located entirely within the interior cavity. The sensor electronics includes an optical power converter configured to convert the light energy communicated from the optical fiber to the optical power converter within the interior cavity via the fiber optic connection port. The light energy is converted into DC electrical energy. The sensor electronics includes an energy storage device configured to store the converted DC electrical energy. The sensor electronics includes a signal generator configured to generate, using at least a portion of the stored DC electrical energy, an electrical excitation signal for use by the vibrating spool transducer. The sensor electronics includes a transducer controller configured to supply the generated electrical excitation signal to the vibrating spool transducer and to determine a resonant frequency of the vibrating spool transducer. The determined resonant frequency is indicative of the density of the fuel. The sensor electronics also includes an optical signal generator configured to generate a light signal, based on the determined resonant frequency, the light signal indicative of the density of the fuel.

DETAILED DESCRIPTION

Figure 1:
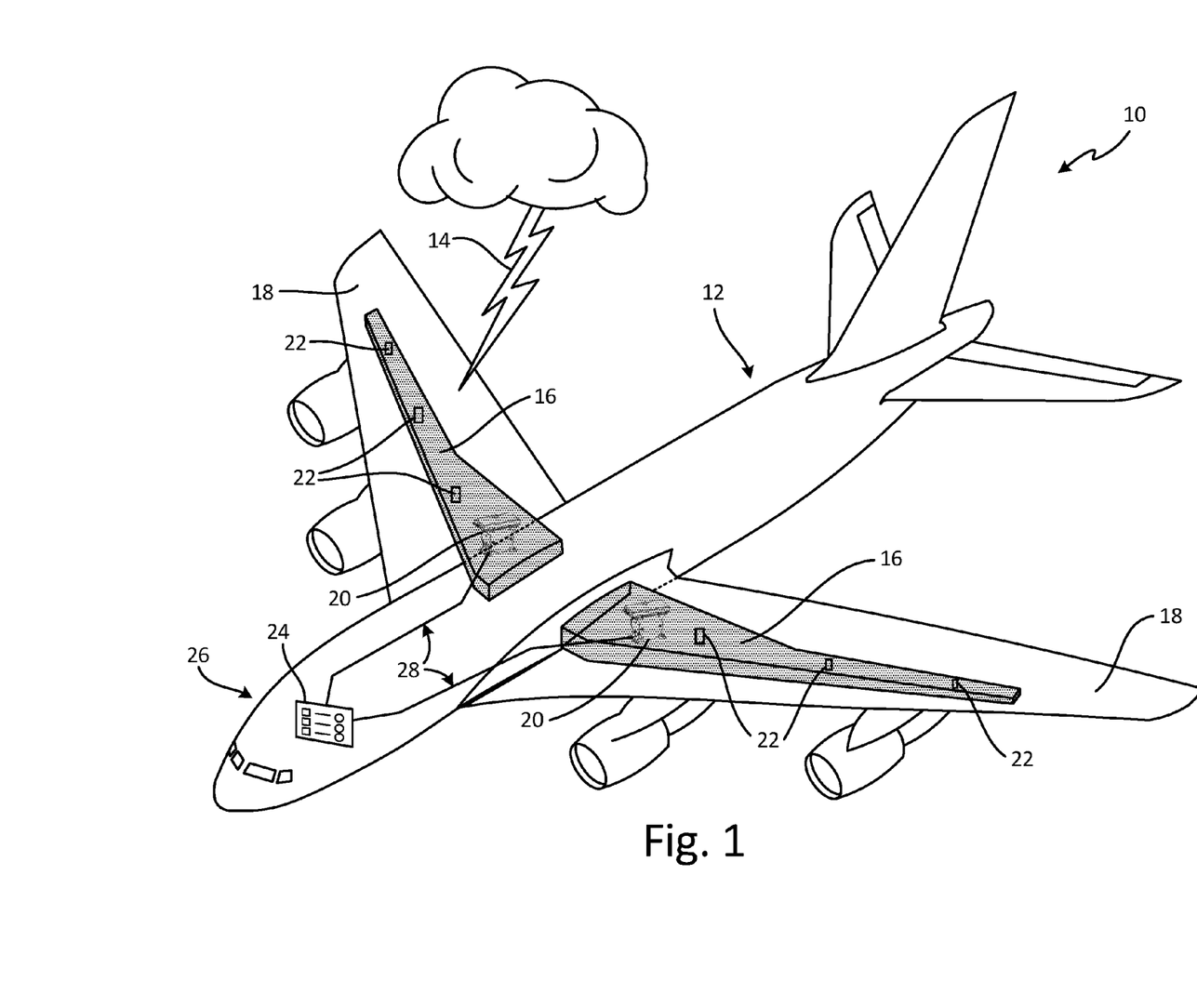
FIG. 1 is a schematic diagram of an exemplary fuel density sensor located within a wing tank of an aircraft.

FIG. 1 is a schematic diagram of an exemplary fuel density sensor located within a wing tank of an aircraft. In FIG. 1, scenario 10 depicts aircraft 12 being struck by lightning bolt 14. Aircraft 12 has fuel tanks 16 in each of wings 18. Within each of fuel tanks 16 are fuel density sensor 20 and fuel volume sensor 22. Fuel density sensors 20 and fuel volume sensors 22 may be in communication with fuel monitoring system 24 located in cockpit 26 of aircraft 12. Fuel density sensors 20 may communicate a measure of density of the fuel within fuel tanks 16 via interconnect 28. If interconnect 28 were a conductive wire type of interconnect, a large voltage and/or current could be coupled onto interconnect 28 in response to lightning bolt 14. A conductive wire type of interconnect could then carry such a large coupled voltage and/or current into fuel tanks 16. In this way, such a conductive wire type of interconnect can present a dangerous risk of igniting the fuel within fuel tanks 16. If interconnect 28 were instead an optical fiber type of interconnect, such voltages and/or currents would not be conductively carried into fuel tanks 16, as optical fibers can have very low electrical conductivities.

A fixed quantity of aircraft fuel may have a volume that changes in response to various factors. For example, the volume may increase in response to increasing temperature and/or decreasing pressure. When the volume increases in such a manner, the density of the fuel decreases such that the product of the density and the volume is substantially constant. Thus, such a product of volume and density may be calculated to provide an accurate measure of the mass of fuel within fuel tanks 16. Fuel monitoring system 24 may combine signals communicated from fuel density sensors 20 and fuel volume sensors 22 to calculate the mass of the fuel contained within fuel tanks 16. For example, the product of a measure of the volume of the fuel within fuel tanks 16 and a measure of the density of the fuel within fuel tanks 16 is a measure of a mass of the fuel within fuel tanks 16. Such a measurement may be an important datum to provide to a pilot. The importance of this datum, however, is not so great as to justify compromising aircraft's 10 ability to tolerate lighting strikes or short circuit failures. Thus, optically interfacing between fuel density sensors 20 and fuel monitoring system 24 advantageously permits calculation of this important datum while minimizing a risk of electrical arcing within fuel tanks 16.

Fuel density sensors 20 may measure a density of the fuel within fuel tanks 16 using various techniques. One such technique is by measuring a resonant frequency of a vibration or oscillating object immersed in the fuel within fuel tanks 16. The principle of operation of many such fuel density measurement devices is that the resonant frequency changes in response to changes in the density of the fuel in which the fuel density measurement device resides. A vibrating spool densitometer is one such fuel density measurement device which operates according to this principle. Some vibrating spool densitometers are electromechanical devices and therefore require electrical operating power and generate an electrical signal indicative of the density of the fuel in which the vibrating spool densitometer resides. Thus, an optical interface should communicate both operating power to the vibrating spool densitometer and a signal indicative of the density measurement from the vibrating spool densitometer.

Figure 2:
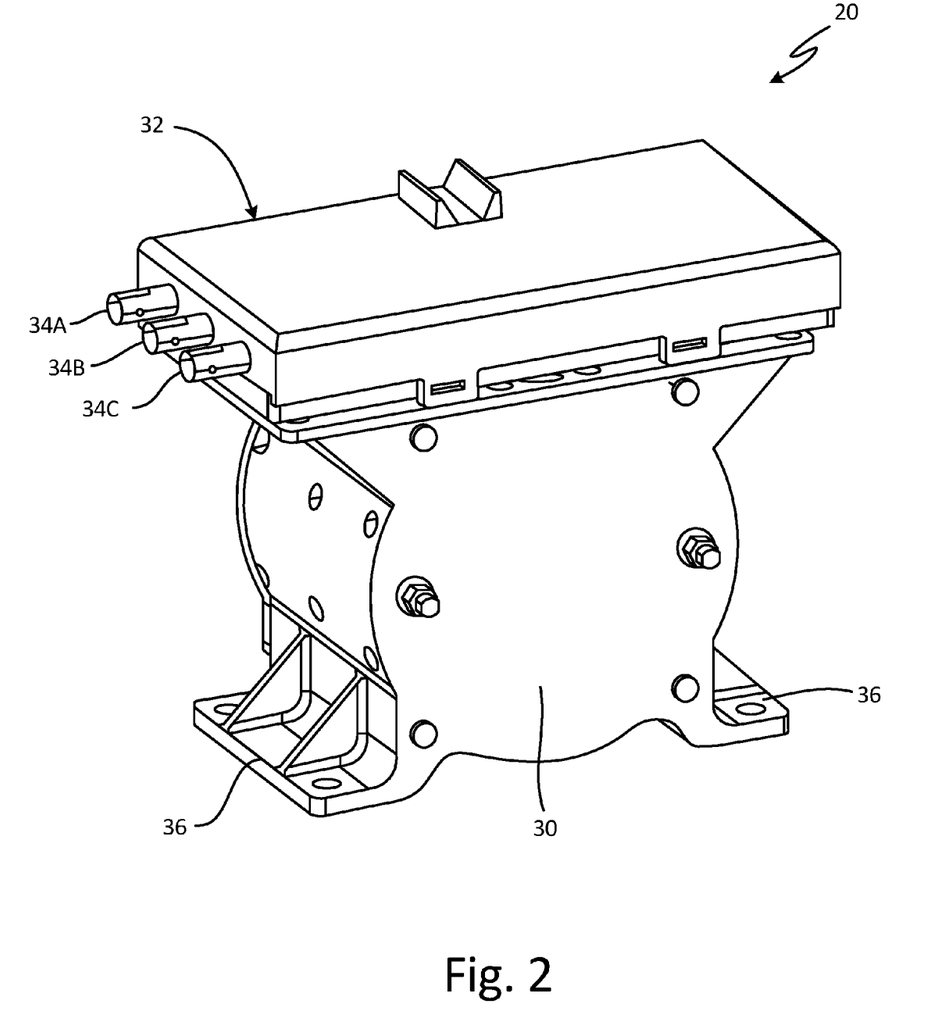
FIG. 2 is a perspective view of an exemplary optically interfaced fluid density sensor.

FIG. 2 is a perspective view of an exemplary optically interfaced fluid density sensor. In FIG. 2, a vibrating spool densitometer type of fuel density sensor 20 is depicted. Exemplary vibrating spool densitometer 20 includes vibrating spool transducer 30, fuel tight housing 32 and fiber optic connection ports 34A-C. Within fuel tight housing 32 is a sensor electronics module. Vibrating spool transducer 30 may be mounted within fuel tank 16 via mounting flanges 36. Vibrating spool transducer 30 may be mounted at locations (e.g., at or near a lower region of a fuel tank) that may contain fuel even in low fuel conditions, such that vibrating spool transducer 30 remains submerged in the fuel of fuel tank 16. When so submerged, accurate measurements of fuel density can be made.

Fuel tight housing 32 provides a physical barrier to fuel, thereby preventing fuel from fuel tank 16 entering an interior cavity, in which the sensor electronics is located. Fuel tight housing 32 may be of a clamshell style two-piece construction, for example. An O-ring and/or gasket made of a material that can withstand exposure to fuel may form a seal between the two pieces of such a construction. Fuel tight housing 32 may electrically isolate the sensor electronics within the cavity from potential high voltage hazards without the cavity. For example, fuel tight housing 32 may three-dimensionally surround the interior cavity within a dielectric material. In such a configurations, there will be no conductive feed through paths from an outside surface to an inside surface of fuel tight housing 32.

Fuel tight housing 32 may be formed of dielectric material fully surrounding the internal cavity. Fuel tight housing 32 may be made of one type of dielectric material or of two or more types of dielectric materials, for example. Fuel tight housing 32 may form a contiguous and gapless dielectric barrier surrounding the cavity that contains the sensor electronics. A thickness and a material may be chosen to meet a dielectric breakdown specification. For example, the dielectric breakdown of the fuel tight housing may be 1000 Volts, or 5000 Volts, or 8000 Volts. The dielectric breakdown specification may be selected to be that of an expected value necessary to withstand an anticipated hazard, such as a lightning strike.

In the depicted embodiment, vibrating spool densitometer 20 has three fiber optic connection ports. In some embodiments, a light energy sufficient for to provide operating power to vibrating spool densitometer 20 may require one, two, or more optical fibers to communicate from the optical fibers to an electronic system within the cavity. In some embodiments, one or more optical fibers may be dedicated to providing operating power to vibrating spool densitometer 20, while one or more optical fibers may be dedicated to providing signal communication between vibrating spool densitometer 20 and an external controller. In some embodiments, both operating power and signal communication may share one or more optical fibers.

In an exemplary embodiment, a single optical fiber communicates operating power from a controller to the vibrating spool densitometer 20 as well as providing signal communication between the controller and vibrating spool densitometer 20. Signal communication may include communication of an output signal from vibrating spool densitometer 20 to the controller of an output signal indicative of a density of a fuel. Signal communication may include communication of a control signal and/or a request signal from the controller to vibrating spool densitometer 20, for example.

Figure 3:
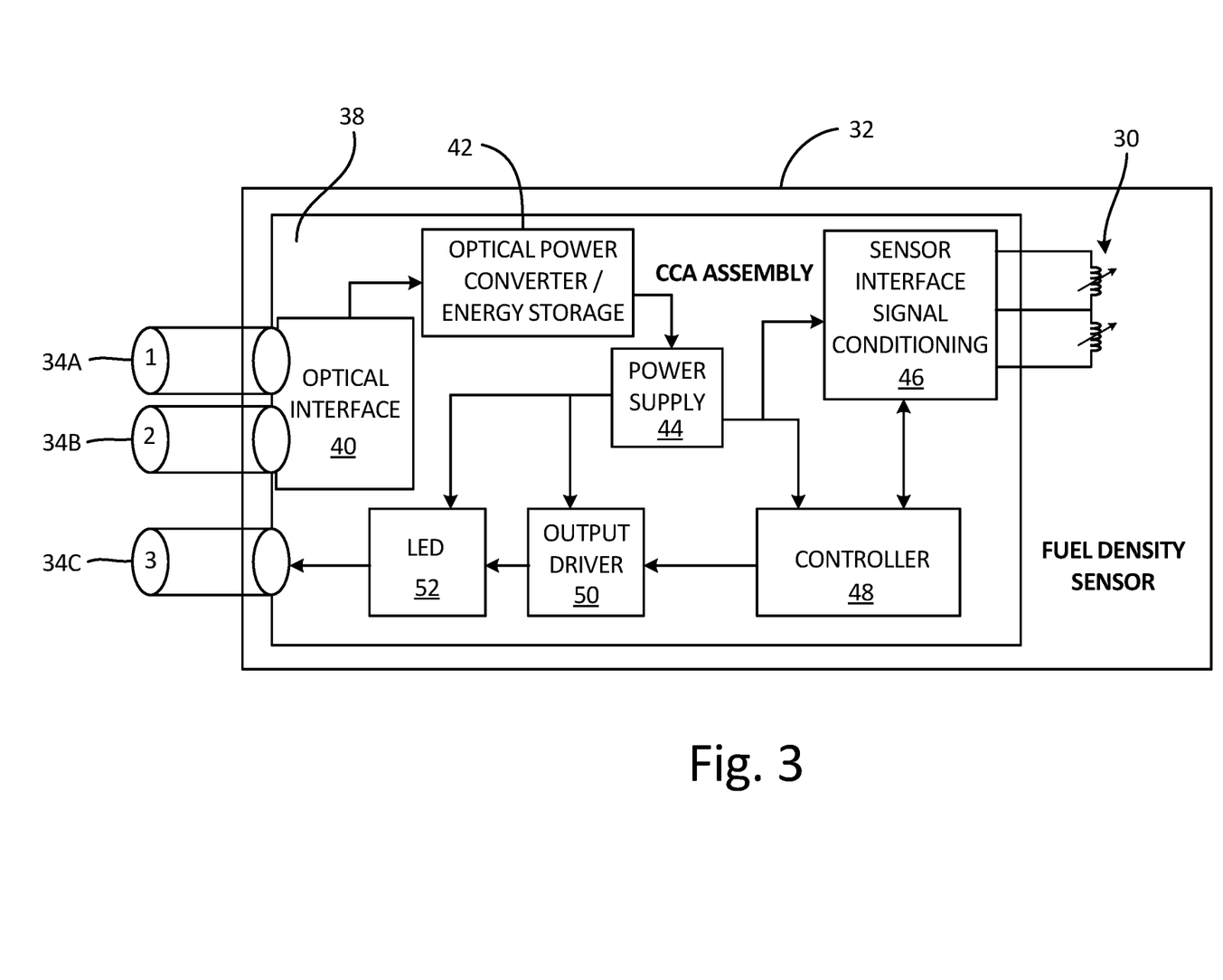
FIG. 3 is a block diagram of an exemplary optically interfaced fluid density sensor.

FIG. 3 is a block diagram of an exemplary optically interfaced fluid density sensor. In FIG. 3, vibrating spool densitometer 20 includes vibrating spool transducer 30, fuel tight housing 32 and fiber optic connection ports 34A-C. Within fuel tight housing 32 is sensor electronics module 38. Sensor electronics module 38 includes: optical interface 40; optical power converter/energy storage module 42; power supply 44; sensor interface/signal conditioning module 46; controller 48; output driver 50; and LED 52.

In the depicted embodiment, optical interface 40 facilitates communication of light energy from fiber optic connection ports 34A-B to optical power converter/energy storage module 42. In some embodiments, optical interface 40 may facilitate communication of light energy from more than two fiber optic connection port. In an exemplary embodiment, optical interface 40 may facilitate communication of light energy from only one fiber optic connection port. In some embodiments, optical interface 40 may facilitate bidirectional communication of light energy between one or more fiber optic connection ports and various electronic and/or optical components located within fuel tight housing 32.

Figure 4:
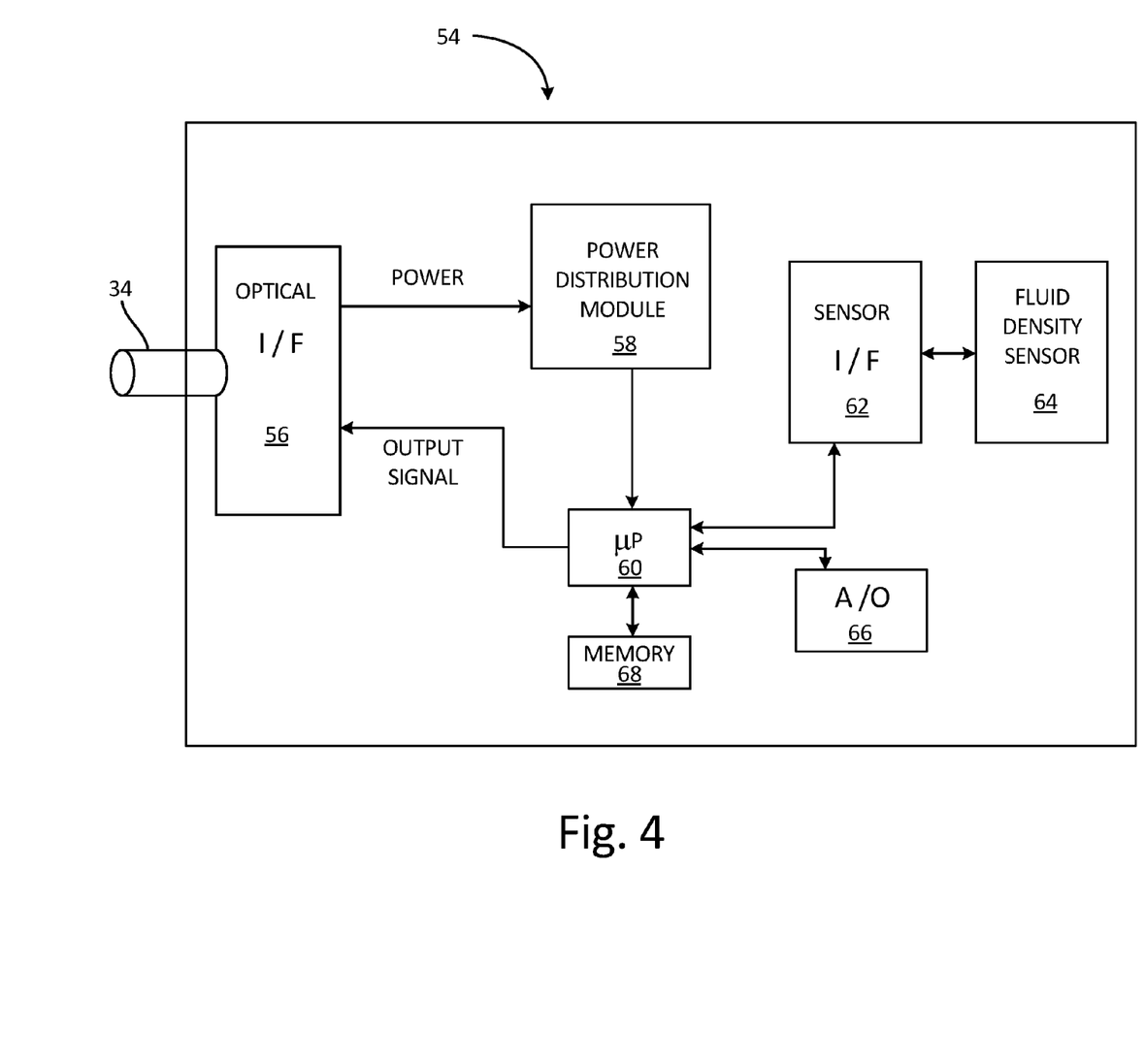
FIG. 4 is a block diagram of an exemplary optically interfaced fluid density sensor.

FIG. 4 is a block diagram of an exemplary optically interfaced fluid density sensor. In FIG. 4, fluid density sensor 54 represents a different embodiment than the embodiment depicted in FIG. 3. The FIG. 4 embodiment includes: optical interface 56; power distribution module 58; microprocessor 60; sensor interface 62; fluid density sensor 64; analog-to-digital converter 66; and memory 68. In the depicted embodiment, optical interface 56 may facilitate bidirectional communication of light energy to and from a single optical fiber connected to fiber optic connection port 34.

Optical operating power can be communicated from the optical fiber connected to fiber optic connection port 34 to power distribution module 58 via optical interface 56. Optical interface 56 may receive light energy from the optical fiber connected to fiber optic connection port 34 and convert the received light energy to electrical energy. In an exemplary embodiment, optical interface 56 may include one or more photo voltaic cells to convert light energy to electrical energy.

Optical interface 56 facilitates communication of an output signal generated by optically interfaced fuel density sensor 54 to an external receiver. Optical interface 56 may receive an electrical output signal indicative of a fluid density from microprocessor 60. Optical interface 56 may generate an optical output signal, based on the received electrical output signal, and transmit the generated optical output signal to an optical fiber connected to fiber optic connection port 34. In some embodiments, optical interface 56 may facilitate other communications between an external controller connected to optically interface fluid density sensor 54 via one or more optical fibers. In some embodiments, optical interface 56 may facilitate bidirectional communication of control signals, measured metrics, and/or software updates, for example.

Light energy converted by optical interface 56 into electrical energy may be electrically conducted to power distribution module 58. Power distribution module 58 may provide for storage of electrical energy provided by optical interface 56. For example, power distribution module 58 may capacitively store electrical energy. Power distribution module 58 may include one or more batteries for storage of electrical energy. Power distribution module 58 may provide charging of one or more batteries when received electrical energy is greater than energy requirements of circuitry to which power distribution module 58 provides operating power. Power distribution module 58 may convert electrical energy from one voltage to one or more different voltages that may be required by circuitry to which power distribution module 58 provides operating power. For example, power distribution module may include a buck and/or boost switched power converter.

Microprocessor 60 may receive operating power from power distribution module 58. Microprocessor 60 may receive program instructions from program memory locations within memory 68. Microprocessor may execute the received program instructions so as to provide an output signal indicative of a fluid density. And to that end, microprocessor may coordinate operations of various optical and/or electronic modules of optically interfaced fluid density sensor 54. Microprocessor may communicate with sensor interface 62 to coordinate signal between sensor interface 62, fluid density sensor 64, and/or analog-to-digital converter 66, for example. Microprocessor 60 and/or sensor interface 62 may, for example, have a phase-lock loop for measuring a resonant frequency of fluid density sensor 64. Microprocessor 60 may save data collected from various optical and/or electrical components in data memory of memory 68.

Figure 5A:
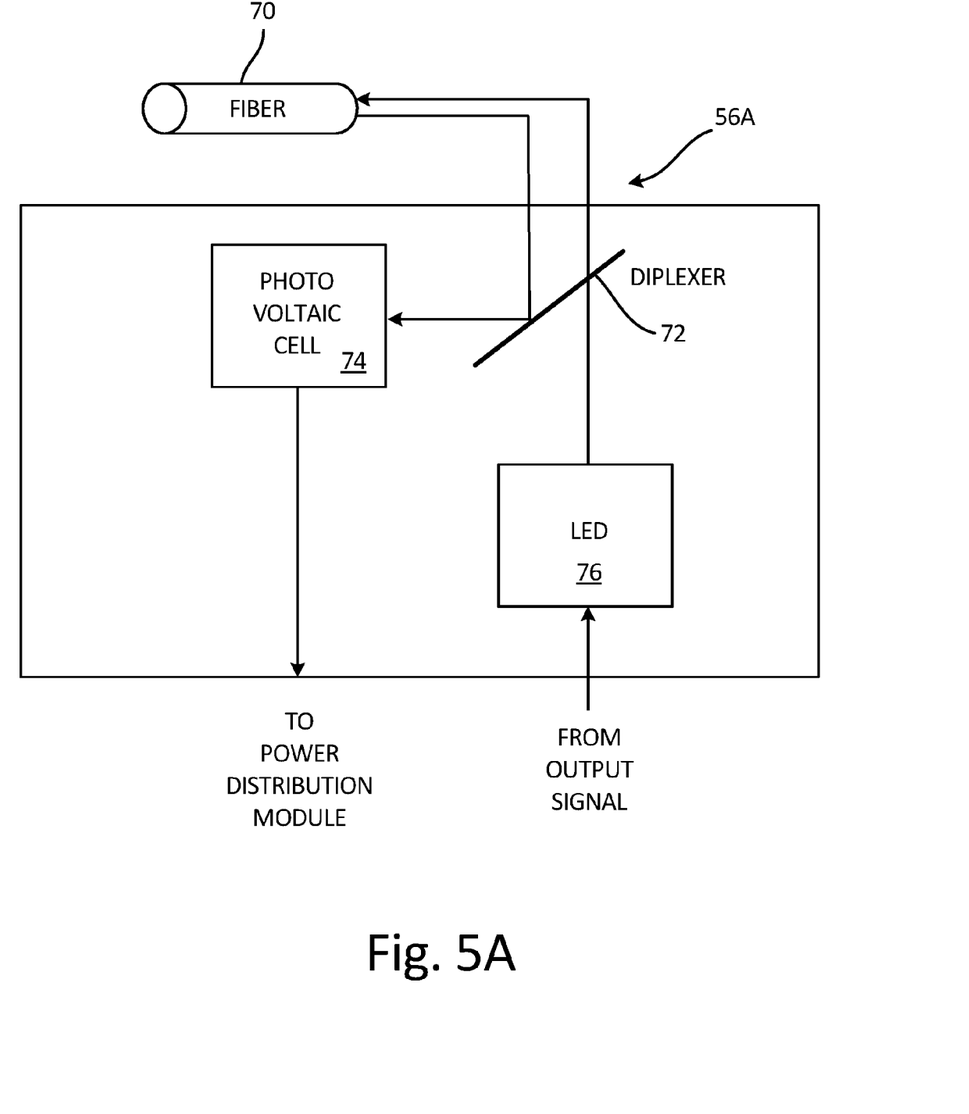
FIGS. 5A-5B are block diagrams of different embodiments of optical interfaces of an optically interfaced fluid density sensor.
Figure 5B:
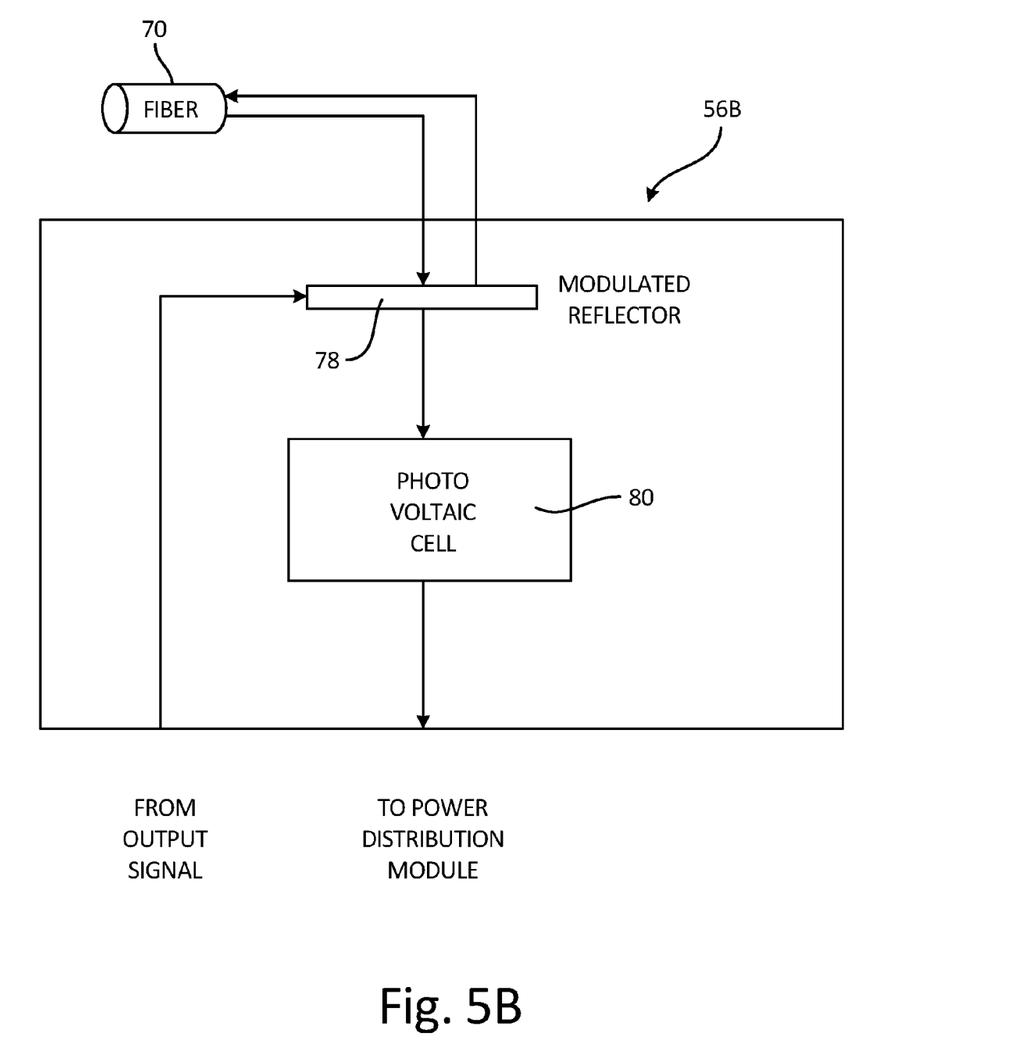

FIGS. 5A-5B are block diagrams of different embodiments of optical interfaces of an optically interfaced fluid density sensor. In FIG. 5A, optical interface 56a is connected to optical fiber 70. Optical interface 56a includes diplexer 72, photo voltaic cell 74 and Light Emitting Diode (LED) 76. Optical fiber 70 may carry light energy to optical interface 56a. Light energy may be directed to photo voltaic cell 74 via diplexer 72. Photo voltaic cell 74 may convert the light energy incident thereon to electrical energy. The converted electrical energy may then be directed to power distribution module 58 (depicted in FIG. 4).

LED 76 may receive an electrical output signal from microprocessor 60 (depicted in FIG. 4). LED may generate an optical output signal in response to the received electrical output signal. The generated optical output signal may then be directed to optical fiber 70 via diplexer 72. Optical fiber 70 may carry light energy for use as operating power to optical interface 56a while providing an optical path for optical output signal from optical interface 56a. Such bidirectional communication can be performed simultaneously or can be performed in a time multiplexed manner. In some embodiments, command signals may also be transmitted by optical fiber 70 from a remote controller to optical interface 56a.

In FIG. 5B, optical interface 56b depicts an alternate embodiment of optical interface 56 depicted in FIG. 4.

Optical interface 56*b* is optically coupled to optical fiber 70. Optical fiber 70 may transmit light energy from a remote controller to optical interface 56*b*. Optical interface 56*b* has modulated reflector 78 and photo voltaic cell 80. Received light energy is directed to photo voltaic cell 80 via modulated reflector 78. Modulated reflector 78 may have a reflection coefficient that can be modulated by an electrical signal, for example. In the depicted embodiment, the reflection coefficient of modulated reflector 78 is modulated in response to an electrical output signal, which may be provided by microprocessor 60 (depicted in FIG. 4). Modulated reflector may reflect a portion of the received light energy in response to the electrical output signal modulating the reflection coefficient, thereby generating an optical output signal.

In an exemplary embodiment, the reflection coefficient of modulated reflector 28 may be modulated between a low value and a higher value. For example, the reflection coefficient may be modulated between 1% and 10%, for example. A complementary transmission coefficient may correspondingly be modulated between 99% and 90%, respectively. In such an embodiment, a majority of the received light energy may be used to provide electrical operating power to a fluid density measurement system, while a small portion of the received light energy can be reflected as an optical output signal.

The following are non-exclusive descriptions of possible embodiments of the present invention.

A fluid density sensor is configured to optically receive operating power and to optically communicate a measured fluid density. The fluid density sensor includes a fluid tight housing separating an interior cavity from an exterior environment. The fluid tight housing is configured to prevent a fluid from the exterior environment from entering the interior cavity. The fluid density sensor includes a fiber optic connection port configured to connect to an optical fiber in the exterior environment while providing an optical path for light energy to traverse the fluid tight housing. The light energy is communicated between the optical fiber and the interior cavity. The fluid density sensor includes a fluid density transducer in the housing configured to be immersed in the fluid. The fluid density transducer generates an electrical output signal indicative of a density of the fluid. The fluid density sensor also includes sensor electronics located entirely within the interior cavity. The sensor electronics include an optical power converter configured to convert the light energy communicated from the optical fiber via the fiber optic connection port into DC electrical energy. The sensor electronics include an energy storage device configured to store the converted DC electrical energy. The sensor electronics include a signal generator configured to generate, using at least a portion of the stored DC electrical energy, an electrical input signal for use by the fluid density transducer. The sensor electronics include a transducer interface configured to supply the generated electrical input signal to the fluid density transducer and to receive the electrical output signal of the fluid density transducer. The sensor electronics also include an optical signal generator configured to generate a light signal, based on the received electrical output signal. The light signal is indicative of the density of the fluid.

A further embodiment of the foregoing fluid density sensor, wherein the light signal indicative of the density of the fluid can be communicated by the optical signal generator to the optical fiber line via the fiber optic connection port. A further embodiment of any of the foregoing fan drive gear systems, wherein the fiber optic connection port can be a first fiber optic connection port. The optical fiber can be a first optical fiber, and the optical path can be a first optical path. The fluid density transducer can further include a second fiber optic connection port configured to connect to a second optical fiber in the exterior environment while providing a second optical path for light energy to traverse the fluid tight housing. The light energy can be communicated between the second optical fiber and the interior cavity. The light signal indicative of the density of the fluid can be communicated from the optical signal generator to the second fiber optic fiber via the second fiber optic connection port.

A further embodiment of any of the foregoing fan drive gear systems, wherein the fluid density sensor can be a vibrating spool densitometer. A further embodiment of any of the foregoing fan drive gear systems, wherein the optical signal generator can include an LED. A further embodiment of any of the foregoing fan drive gear systems, wherein the optical power converter can include a photo voltaic cell. A further embodiment of any of the foregoing fan drive gear systems, wherein the optical signal generator can be configured to generate a light signal indicative of the density of the fluid by modulating a reflection of the light energy delivered by the optical fiber. The reflected light signal can be communicated by the optical fiber in a direction antiparallel to the direction of the unreflected light energy carried by the optical fiber. A further embodiment of any of the foregoing fan drive gear systems, wherein the fluid tight housing comprises a dielectric material having a dielectric breakdown greater than or equal to 1000 Volts or greater than or equal to 5000 Volts or greater than or equal to 8000 Volts.

A method of suppressing electrical arcing within a fuel tank in which a fuel density sensor is located includes physically isolating sensor electronics from fuel in the fuel tank via a fuel barrier defining a cavity. The method includes electrically isolating the sensor electronics within the cavity from potential high voltage hazards outside the cavity. The method includes optically transmitting a light energy from a first environment outside the cavity to a second environment within the cavity to provide operating power for the sensor electronics. The method includes optically transmitting a light signal from the second environment within the cavity to the first environment outside the cavity. The light signal is indicative of fuel density. The method includes converting the light energy into DC electrical energy within the cavity. The method includes storing the converted DC electrical energy. The method includes supplying the sensor electronics with operating power from the converted DC electrical energy. The method includes determining a density of fuel within the fuel tank outside the cavity. The method also includes generating the light signal indicative of the fuel density.

A further embodiment of the foregoing method of suppressing electrical arcing within a fuel tank in which a fuel density sensor is located, wherein optically transmitting light energy between outside the cavity and within the cavity can include optically transmitting light energy carried by an optical fiber external to the cavity to an optical receiver within the cavity. A further embodiment of any of the foregoing methods, wherein generating the light signal can include modulating an electrical voltage across an LED. A further embodiment of any of the foregoing methods, wherein generating the light signal can include modulating a reflection of light energy transmitted from without the cavity to within the cavity such that a portion of the transmitted light energy is reflected from within the cavity to without the cavity. A further embodiment of any of the foregoing methods, wherein electrically isolating sensor electronics can include electrical isolation withstanding high voltage hazards of 1000 Volts, 5000 Volts or 8000 Volts.

A vibrating spool densitometer is configured to optically receive operating power and to optically communicate a measured fuel density. The vibrating spool densitometer includes a fuel tight housing separating an interior cavity from an exterior environment. The fuel tight housing is configured to prevent a fuel from the exterior environment from entering the interior cavity. The vibrating spool densitometer includes a fiber optic connection port configured to connect to an optical fiber in the exterior environment while providing an optical path for light energy to be communicated from the optical fiber to the interior cavity. The vibrating spool densitometer includes a vibrating spool transducer in the housing configured to be immersed in the fuel. The vibrating spool transducer has a resonant frequency indicative of a density of the fuel. The vibrating spool densitometer also includes sensor electronics located entirely within the interior cavity. The sensor electronics include an optical power converter configured to convert the light energy communicated from the optical fiber via the fiber optic connection port into DC electrical energy. The sensor electronics include an energy storage device configured to store the converted DC electrical energy. The sensor electronics include a signal generator configured to generate, using at least a portion of the stored DC electrical energy, an electrical excitation signal for use by the vibrating spool transducer. The sensor electronics include a transducer controller configured to supply the generated electrical excitation signal to the vibrating spool transducer and to determine a resonant frequency of the vibrating spool transducer. The determined resonant frequency is indicative of the density of the fuel. The sensor electronics also includes an optical signal generator configured to generate a light signal, based on the determined resonant frequency. The light signal is indicative of the density of the fuel.

A further embodiment of the foregoing vibrating spool densitometer, wherein the light signal indicative of the density of the fuel can be communicated by the optical signal generator to the optical fiber line via the fiber optic connection port. A further embodiment of any of the foregoing vibrating spool densitometers, wherein the fiber optic connection port is a first fiber optic connection port, the optical fiber is a first optical fiber, and the optical path is a first optical path. The vibrating spool densitometer can further include a second fiber optic connection port configured to connect to a second optical fiber in the exterior environment while providing a second optical path for light energy to traverse the fuel tight housing. The light energy can be communicated between the second optical fiber and the interior cavity. The light signal can be indicative of the density of the fuel is communicated from the optical signal generator to the second fiber optic line via the second fiber optic connection port. A further embodiment of any of the foregoing vibrating spool densitometers, wherein the optical signal generator comprises an LED. A further embodiment of any of the foregoing vibrating spool densitometers, wherein the optical signal generator is configured to generate a light signal indicative of the density of the fuel by modulating a reflection of the light energy delivered by the optical fiber, the reflected light signal is communicated by the optical fiber in a direction antiparallel to the direction of the unreflected light energy carried by the optical fiber.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A fluid density sensor configured to optically receive operating power and to optically communicate a measured fluid density, the fluid density sensor comprising:
  a fluid tight housing separating an interior cavity from an exterior environment, the fluid tight housing configured to prevent a fluid from the exterior environment from entering the interior cavity;
  a fiber optic connection port configured to connect to an optical fiber in the exterior environment while providing an optical path for light energy to traverse the fluid tight housing, the light energy communicated between the optical fiber and the interior cavity;
  a fluid density transducer in the housing configured to be immersed in the fluid, the fluid density transducer generating an electrical output signal indicative of a density of the fluid; and
  sensor electronics located entirely within the interior cavity, the sensor electronics comprising:
    an optical power converter configured to convert the light energy communicated from the optical fiber via the fiber optic connection port into DC electrical energy;
    an energy storage device configured to store the converted DC electrical energy;
    a signal generator configured to generate, using at least a portion of the stored DC electrical energy, an electrical input signal for use by the fluid density transducer;
    a transducer interface configured to supply the generated electrical input signal to the fluid density transducer and to receive the electrical output signal of the fluid density transducer; and
    an optical signal generator configured to generate a light signal, based on the received electrical output signal, the light signal indicative of the density of the fluid,
    wherein the optical signal generator is configured to generate a light signal indicative of the density of the fluid by modulating a reflection of the light energy delivered by the optical fiber, and the reflected light signal is communicated by the optical fiber in a direction antiparallel to the direction of the unreflected light energy carried by the optical fiber.

2. The fluid density sensor of claim 1, wherein the light signal indicative of the density of the fluid is communicated by the optical signal generator to the optical fiber line via the fiber optic connection port.

3. The fluid density sensor of claim 1, wherein the fiber optic connection port is a first fiber optic connection port, the optical fiber is a first optical fiber, and the optical path is a first optical path, the fluid density transducer further comprising:
  a second fiber optic connection port configured to connect to a second optical fiber in the exterior environment while providing a second optical path for light energy to traverse the fluid tight housing, the light energy communicated between the second optical fiber and the interior cavity, wherein the light signal indicative of the density of the fluid is communicated from the optical signal generator to the second fiber optic fiber via the second fiber optic connection port.

4. The fluid density sensor of claim 1, wherein the fluid density sensor is a vibrating spool densitometer.

5. The fluid density sensor of claim 1, wherein the optical power converter comprises a photo voltaic cell.

6. The fluid density sensor of claim 1, wherein the fluid tight housing comprises a dielectric material having a dielectric breakdown greater than or equal to 1000 Volts.

7. The fluid density sensor of claim 1, wherein the fluid tight housing comprises a dielectric material having a dielectric breakdown greater than or equal to 5000 Volts.

8. The fluid density sensor of claim 1, wherein the fluid tight housing comprises a dielectric material having a dielectric breakdown greater than or equal to 8000 Volts.

9. A method of suppressing electrical arcing within a fuel tank in which a fuel density sensor is located, the method comprising:
   physically isolating sensor electronics from fuel in the fuel tank via a fuel barrier defining a cavity;
   electrically isolating the sensor electronics within the cavity from potential high voltage hazards outside the cavity;
   optically transmitting a light energy from a first environment outside the cavity to a second environment within the cavity to provide operating power for the sensor electronics;
   optically transmitting a light signal from the second environment within the cavity to the first environment outside the cavity, the light signal indicative of fuel density;
   converting the light energy into DC electrical energy within the cavity;
   storing the converted DC electrical energy;
   supplying the sensor electronics with operating power from the converted DC electrical energy;
   determining a density of fuel within the fuel tank outside the cavity; and
   generating the light signal indicative of the fuel density,
   wherein the light signal comprises modulating a reflection of light energy transmitted from without the cavity to within the cavity such that a portion of the transmitted light energy is reflected from within the cavity to without the cavity.

10. The method of claim 9, wherein optically transmitting light energy between outside the cavity and within the cavity comprises optically transmitting light energy carried by an optical fiber external to the cavity to an optical receiver within the cavity.

11. The method of claim 9, wherein electrically isolating sensor electronics comprises electrical isolation withstanding high voltage hazards of 8000 Volts.

12. A vibrating spool densitometer configured to optically receive operating power and to optically communicate a measured fuel density, the vibrating spool densitometer comprising:
   a fuel tight housing separating an interior cavity from an exterior environment, the fuel tight housing configured to prevent a fuel from the exterior environment from entering the interior cavity;
   a fiber optic connection port configured to connect to an optical fiber in the exterior environment while providing an optical path for light energy to be communicated from the optical fiber to the interior cavity;
   a vibrating spool transducer in the housing configured to be immersed in the fuel, the vibrating spool transducer having a resonant frequency indicative of a density of the fuel; and
   sensor electronics located entirely within the interior cavity, the sensor electronics comprising:
      an optical power converter configured to convert the light energy communicated from the optical fiber via the fiber optic connection port into DC electrical energy;
      an energy storage device configured to store the converted DC electrical energy;
      a signal generator configured to generate, using at least a portion of the stored DC electrical energy, an electrical excitation signal for use by the vibrating spool transducer;
      a transducer controller configured to supply the generated electrical excitation signal to the vibrating spool transducer and to determine a resonant frequency of the vibrating spool transducer, the determined resonant frequency indicative of the density of the fuel; and
      an optical signal generator configured to generate a light signal, based on the determined resonant frequency, the light signal indicative of the density of the fuel,
   wherein the optical signal generator is configured to generate a light signal indicative of the density of the fuel by modulating a reflection of the light energy delivered by the optical fiber, the reflected light signal is communicated by the optical fiber in a direction antiparallel to the direction of the unreflected light energy carried by the optical fiber.

13. The vibrating spool densitometer of claim 12, wherein the light signal indicative of the density of the fuel is communicated by the optical signal generator to the optical fiber line via the fiber optic connection port.

14. The vibrating spool densitometer of claim 12, wherein the fiber optic connection port is a first fiber optic connection port, the optical fiber is a first optical fiber, and the optical path is a first optical path, the vibrating spool densitometer further comprising:
   a second fiber optic connection port configured to connect to a second optical fiber in the exterior environment while providing a second optical path for light energy to traverse the fuel tight housing, the light energy communicated between the second optical fiber and the interior cavity,
   wherein the light signal indicative of the density of the fuel is communicated from the optical signal generator to the second fiber optic line via the second fiber optic connection port.

* * * * *